United States Patent
White et al.

(10) Patent No.: US 7,799,046 B2
(45) Date of Patent: Sep. 21, 2010

(54) DYNAMIC CANNULA

(75) Inventors: Jennifer Keane White, Brookline, MA (US); James Sidney Titus, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 1643 days.

(21) Appl. No.: 10/498,442

(22) PCT Filed: Dec. 16, 2002

(86) PCT No.: PCT/US02/40349

§ 371 (c)(1),
(2), (4) Date: Jun. 10, 2004

(87) PCT Pub. No.: WO2004/054650

PCT Pub. Date: Jul. 1, 2004

(65) Prior Publication Data

US 2005/0107817 A1    May 19, 2005

Related U.S. Application Data

(60) Provisional application No. 60/341,357, filed on Dec. 14, 2001.

(51) Int. Cl.
*A61M 29/00* (2006.01)
(52) U.S. Cl. .................................... 606/191
(58) Field of Classification Search ......... 606/191–198, 606/151, 157, 200, 33, 40, 49; 623/1.11, 623/1.12; 604/104–107, 164, 64
See application file for complete search history.

(56) References Cited

U.S. PATENT DOCUMENTS

| | | | | |
|---|---|---|---|---|
| 5,041,093 A | * | 8/1991 | Chu | 604/104 |
| 5,573,517 A | | 11/1996 | Bonutti et al. | |
| 5,911,702 A | | 6/1999 | Romley et al. | |
| 6,165,172 A | * | 12/2000 | Farley et al. | 606/33 |
| 6,190,357 B1 | * | 2/2001 | Ferrari et al. | 604/102.01 |
| 6,210,370 B1 | | 4/2001 | Chi-Sing et al. | |
| 6,340,356 B1 | | 1/2002 | Navia et al. | |
| 2002/0010440 A1 | | 1/2002 | Segesser | |
| 2002/0065530 A1 | | 5/2002 | Mische | |

FOREIGN PATENT DOCUMENTS

| | | |
|---|---|---|
| EP | 0 385 920 | 9/1990 |
| WO | WO 99/55285 | 11/1999 |
| WO | WO 01/52753 | 7/2001 |

OTHER PUBLICATIONS

Wareing et al., "Management of severely atherosclerotic ascending aorta during cardiac operations," J. Thorac. Cardiovasc. Surg. 103:462 (1992).

(Continued)

*Primary Examiner*—Kevin T Truong
(74) *Attorney, Agent, or Firm*—Fish & Richardson P.C.

(57) ABSTRACT

A perfusion cannula constructed of a wire mesh or other structure having an expandable portion capable of expanding from a constricted state to an expanded state such that a vessel is stented open while permitting fluid flow through a cannula into the vessel.

36 Claims, 22 Drawing Sheets

OTHER PUBLICATIONS

Brodman et al., "A Comparison of Flow Gradients across Disposable Arterial Perfusion Cannulas," Ann. Thor. Surg. 39:225-33 (1984).

Harshbarger et al., "Studies in extracorporeal circulation. IV. Surgical techniques," Surg. Gynecol. Obstet. 106(1):111-118 (1958).

Muehrcke et al., "Flow characteristics of aortic cannulae," J. Card. Surg. 10(4 Suppl):514-519 (1995).

Pfaender, L.M., "Hemodynamics in the extracorporeal Aortic Cannula: Review of Factors Affecting Choice of the Appropriate Size," J. Extra-Corporeal Technol. 13:224-32 (1981).

Reichenspurner and Navia, "Emboli management with a novel aortic filtration system: histopatholoical confirmation of atheromatous plaque capture in cardiac surgery," AATS, $79^{th}$ Annual meeting, Apr. 18-21, 1999, New Orleans, LA.

Roach et al., "Adverse cerebral outcomes after coronary bypass surgery. Multicenter Study of Perioperative Ischemia Research Group and the Ischemia Research and Education Foundation Investigators," N. Engl. J. Med. 335(25):1857-63 (1996).

Verdonck et al., "Hydrodynamical comparison of aortic arch cannulae," Int. J. Artif. Organs. 21(11):705-13 (1998).

Borger et al., "Decreased cerebral emboli during distal aortic arch cannulation: a randomized clinical trial," J. Thorac. Cardiovasc. Surg. 118(4):740-5 (1999).

Hwang et al., "Hydraulic Studies of Aortic Cannulation Return Nozzles," Trans. Amer. Soc. Artif. Int. Organs XXI:234-237 (1975).

Benaroia et al., "Effect of aortic cannula characteristics and blood velocity on transcranial doppler-detected microemboli during cardiopulmonary bypass," J. Cardiothorac. Vasc. Anesth. 12(3):266-9 (1998).

Hamano et al., "Atheromatous plaque in the distal aortic arch creating the potential for cerebral embolism during cardiopulmonary bypass," Jpn. Circ. J. 65(3):161-4 (2001).

Delius et al., "New method for describing the performance of cardiac surgery cannulas," Ann. Thorac. Surg. 53(2):278-81 (1992).

Rodriguez et al., "Cerebral vascular effects of aortovenous cannulations for pediatric cardiopulmonary bypass," Ann. Thorac. Surg. 69(4):1229-35 (2000).

Grossi et al., "Effect of cannula length on aortic arch flow: protection of the atheromatous aortic arch," Ann. Thorac. Surg. 59(3):710-2 (1995).

Müllges et al., "Brain microembolic counts during extracorporeal circulation depend on aortic cannula position," Ultrasound Med. Biol. 27(7):933-6 (2001).

Joubert-Huebner et al., "An in vitro evaluation of a new cannula tip design compared with two clinically established cannula-tip designs regarding aortic arch vessel perfusion characteristics," Perfusion 15(1):69-76 (2000).

Curtis et al., "Novel ventricular apical cannula: in vitro evaluation using transparent, compliant ventricular casts," ASAIO J. 44(5):M691-5 (1998).

White JK, Titus JS, Fischer JI, Madsen JC, Agnihotri AK, Torchiana DF, "A Novel Arterial Cannula with Radial Expansion Characteristics." Presented at 22nd Annual San Diego Cardiothoracic Surgery Symposium, Pathophysiology and Techniques of Cardiopulmonary Bypass. Feb. 21-23, 2002, San Diego, CA.

* cited by examiner

Figure 11A
Figure 11B
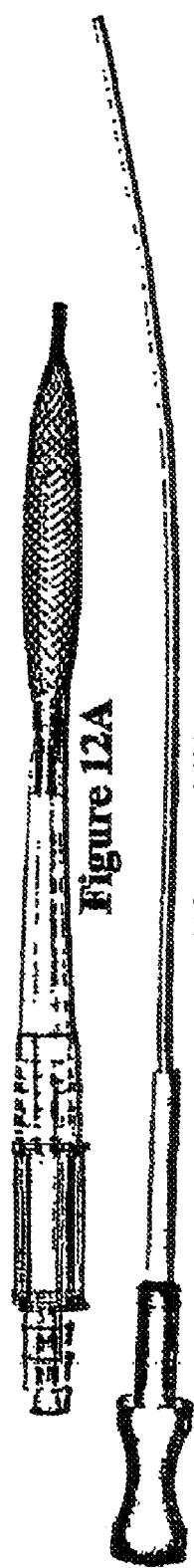
Figure 12A
Figure 12B

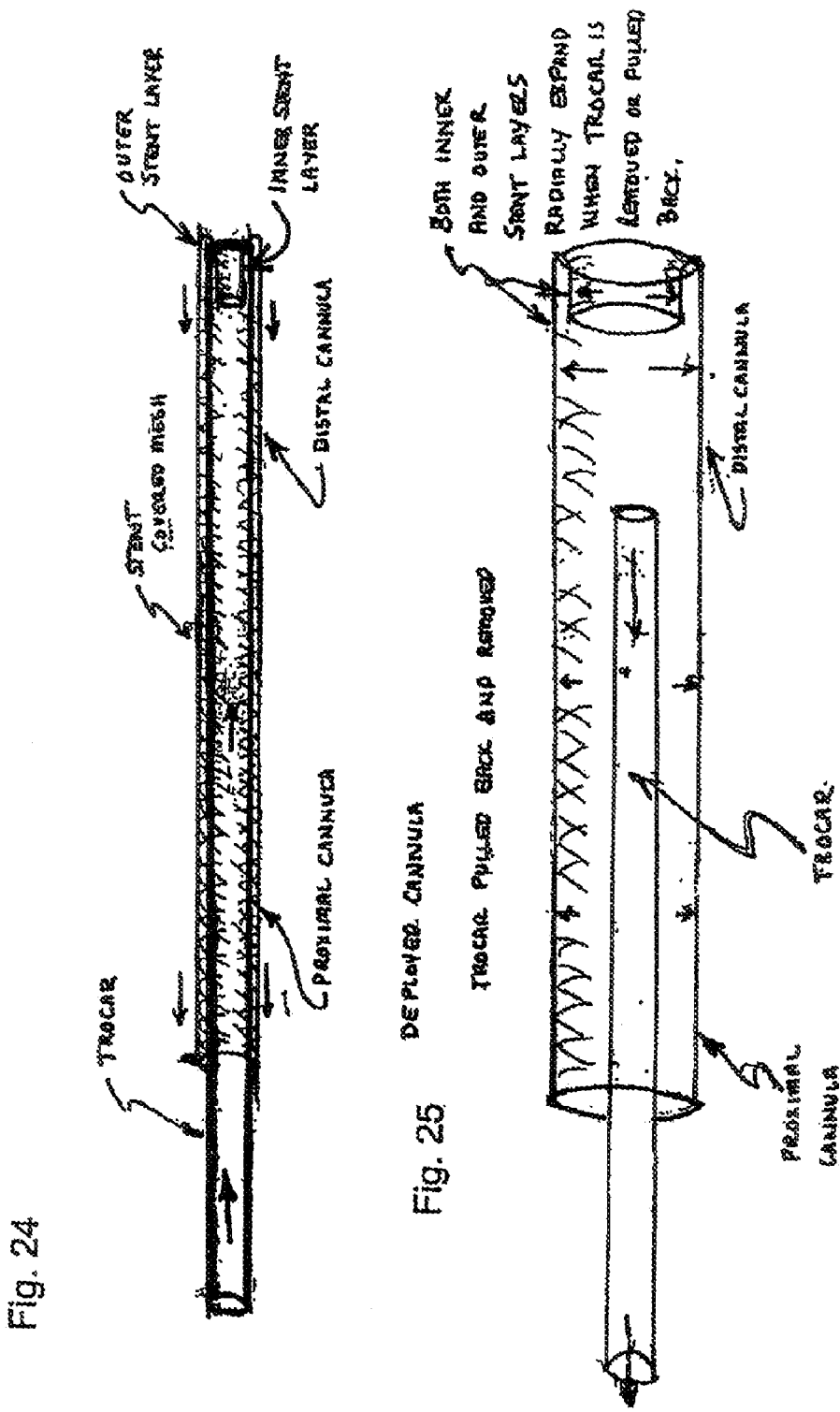

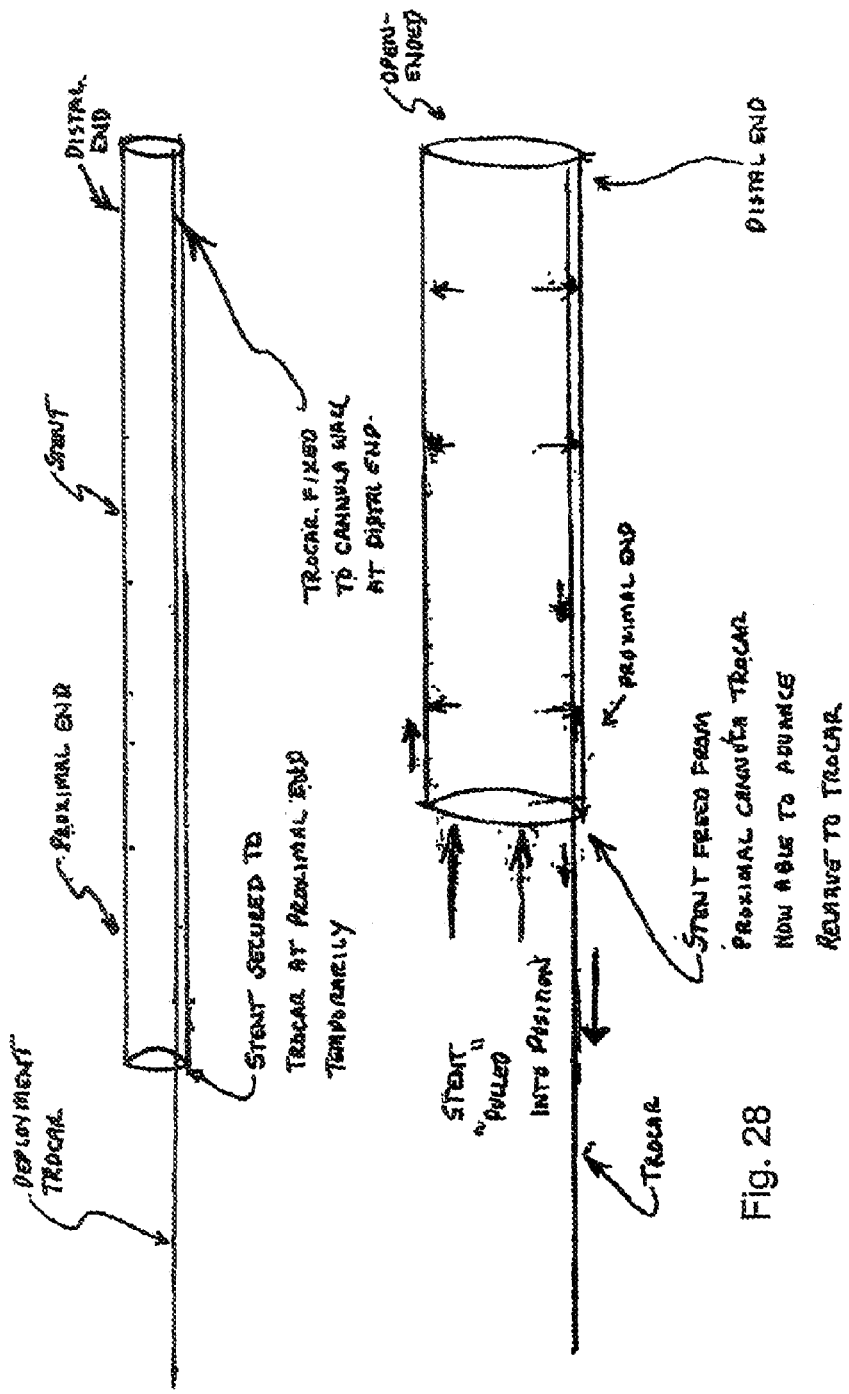

DYNAMIC CANNULA

CROSS REFERENCE TO RELATED APPLICATION

This application claims priority benefit from U.S. Provisional Patent Application No. 60/341,357, filed Dec. 14, 2001, entitled "Dynamic Cannula", the disclosure of which is incorporated herein in its entirety.

FEDERALLY SPONSORED RESEARCH OR DEVELOPMENT

This invention was made with Government support under Grant No. DAMD17-99-2-9001 awarded by the U.S. Department of the Army. The Government has certain rights to the invention.

FIELD OF THE INVENTION

The present invention relates to cannulae and stenting devices with a dynamic radial diameter that permits the device to reversibly expand from a narrower insertion diameter to a larger in-dwelling diameter and provide fluid flow selectively through the device wall.

BACKGROUND OF THE INVENTION

In cardiac surgery, connections between the patient's vasculature and extracorporeal circulation are established and maintained by cannulae that serve as temporary conduits for blood flow. Conventional cannulae are semi-rigid polyvinyl chloride or polyurethane tubes positioned and secured by sutures in the patient's arterial and venous vessels. Since cannulae were first used in human cardiopulmonary bypass in the 1950's, the design of the most widely used arterial and venous cannula has not changed dramatically.

From early usage in the history of cardiac surgery, it has been widely appreciated that cannulae designs that maximize fluid flow are preferred. In general, surgeons purposely select the largest diameter cannula that can be atraumatically inserted into a blood vessel to increase perfusion to the body and drainage to the extracorporeal pump. In addition, utilizing a cannula of greater cross-sectional area reduces damage to blood elements as blood traverses along the cannula wall. Manufacturers have recently reduced the cannula wall thickness and added side-holes in the end of cannulae in attempts to increase flow at the cannula tip. However, less than optimal fluid flow characteristics persist if there are abrupt size discrepancies at any point along the path of blood flow.

Changes in cross-sectional area or shape such as a sudden expansion, contraction, or an angle in the stream of flow cause the fluid velocity to change direction or magnitude. This produces an increase in friction and turbulence as compared to fluid flow in a straight tube. Since cardiopulmonary bypass cannula function to form a connection between standard size extracorporeal tubing and blood vessels that vary in diameter and compliance, significant turbulence may result. The evolution of cannula to more tapered designs and wire reinforcement to prevent sharp angles reflect the attempts by industry to overcome these size and shape discrepancy problems.

At present, industry uses a standardized method to compare fluid flow and turbulence characteristics of various cannula designs by measuring "pressure drop." The pressure drop is determined by measuring the change in pressure as compared to fluid flow perfusing through the cannula in a standardized test apparatus. In practice, each cannula design has a published pressure drop which is made available to the surgeon to allow comparison between cannula designs. Unfortunately, the industry's standard method of measuring the pressure drop provides limited information about fluid flow characteristics within the blood vessel, beyond the distal end of the cannula.

The importance of fluid flow characteristics beyond the cannula tip is exemplified by the so-called "sandblasting" effect described for aortic cannula perfusion during cardiopulmonary bypass. A jet of high velocity blood exiting the relatively small perfusion cannula (approximately 7-8 mm) into the adult ascending aorta (approximately 30 mm) has been identified as a source of dislodgement and mobilization of artherosclerotic atheroma to vital organs. This has been suggested as a potential mechanism of cerebral infarcts in patient's undergoing cardiac surgery. Various devices which include special tip cannula (Sarns softflow® cannula, 3M Healthcare, Ann Arbor, Mich., USA and Edwards DISPERSION® cannula, Research Medical Inc., Midvale, Utah, USA) or temporary filters (EMBOLEX®, Mountain View, Calif., USA) have been proposed to prevent this phenomenon or its associated morbidity.

The performance of cannulae are influenced by the biomechanical properties of the vessels they cannulate. Too rapid drainage of the venous system can cause intermittent collapse of the vein distal to the cannula. This can significantly reduce fluid flow and produces excessive cannula movement referred to as "chattering" as the vein repeatedly collapses and refills. This phenomenon may significantly impede venous drainage and disturb the surgical procedure by disrupting the surgical field with vibration and movement. In order to address this problem, specialized cannulae designed to eliminate collapse of the vein are commercially available, such as the swirl tip atrial caval venous cannula (Medtronic Corporation, Minneapolis, Minn., USA).

Venous cannulae generally tend to be a larger diameter and a longer length than arterial cannula. These design features are intended to compensate for the compliant nature of the veins and prevent vessel collapse. However, the increase in cannula length can significantly increase the resistance of the fluid path. In addition, minimally invasive cardiac surgery has led to a need for smaller diameter venous cannula for use with vacuum-assisted drainage which tends to exacerbate distal vein collapse.

Even with open surgical field exposure, judging the size of blood vessels can be difficult due to fluid pressure changes or vessel spasm following tissue dissection. Cannulation procedures performed with maximal surgical exposure can be less than optimal due to erroneous blood vessel sizing due to fluid pressure changes or vessel spasm during dissection. Minimally invasive cannulation increases the technical challenge of vessel sizing due to limited exposure. Overestimation of the size of the vessel may result in selection of too large of a cannula and excessive vessel trauma during cannulation. Underestimation of blood vessel size with insertion (of a smaller cannula may result in less than optimized fluid flow. Incorrect cannula size selection may delay the procedure and increase discarded, but unusable cannula.

Technological developments are increasingly challenging the limits of current cannula designs. Advancements in extracorporeal devices, such as ventricular assist devices (VAD) have increased the potential for size discrepancies between the patient's vasculature and the circuit. Minimally invasive techniques, such as extracorporeal membrane oxygenation (ECMO) and vacuum-assisted drainage, have increased the use of small peripheral blood vessels as cannulation sites.

Previous attempts have helped to solve narrow parts of the problems discussed above. However, there has not been a broad-spectrum advance in cannula design to address these problems in the wide range of applications in which cannulae are now commonly used. It would be desirable to construct a novel cannula to universally improve fluid dynamics and provide atraumatic insertion of cannula into blood vessels. It would be desirable that the cannula have a narrow insertion profile to ease insertion. Following placement, it would be desirable that a simple mechanism elicit the cannula to possess a wide internal diameter. It would be desirable for the device to exert an atraumatic force on the structures it cannulates to optimize the biomechanics of these structures for fluid flow. It would be desirable to have a cannula that would minimize or eliminate the reduction in fluid flow due to compliant vessel collapse. In certain applications, it would be desirable that the device completely occlude fluid flow through a blood vessel. In other applications, it would be desirable that the cannula selectively filter particles. It would also be desirable to have a single cannula that would replace the need for a number of different diameter cannulae to match the various sizes of the structures it cannulates.

SUMMARY OF THE INVENTION

The present invention provides a number of unique structures and configurations of cannulae which can expand from a first diameter in a constricted state to a second diameter in a relaxed state. An important feature is that when the structure of the present invention is in situ it can be re-constricted to the narrower diameter and either repositioned or removed from the vessel or other site, thereby minimizing potential trauma to the surrounding tissue or structure.

A method of deploying and using the present invention is provided. Also provided is a kit incorporating the cannulae of the present invention.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which:

FIG. 1 shows the insertion of a narrow profile configuration of a cannula. The internal trocar exerts a longitudinal elongation force on the cannula which acts to narrow the cannula's diameter.

FIG. 2 shows the deployment of the cannula by withdrawal of an internal trocar.

FIG. 3 shows the final deployed state of a cannula according to one embodiment of the present invention.

FIG. 11A shows a conventional femoral arterial cannula with a conventional trocar (FIG. 11B) in narrow insertion profile according to one embodiment of the present invention.

FIG. 12A shows a femoral arterial cannula with a conventional trocar (FIG. 12B) removed in expanded profile according to one embodiment of the present invention.

FIG. 24 shows the undeployed cannula depicting double layer cannula with deployment mechanism.

FIG. 25 shows the deployed cannula.

FIG. 27 shows the undeployed cannula depicting deployment trocar call be integral part of stent wall.

FIG. 28 shows the deployed cannula depicting "pulling" vs. pushing into position.

DETAILED DESCRIPTION OF THE INVENTION

Figures 1, 2, 3:
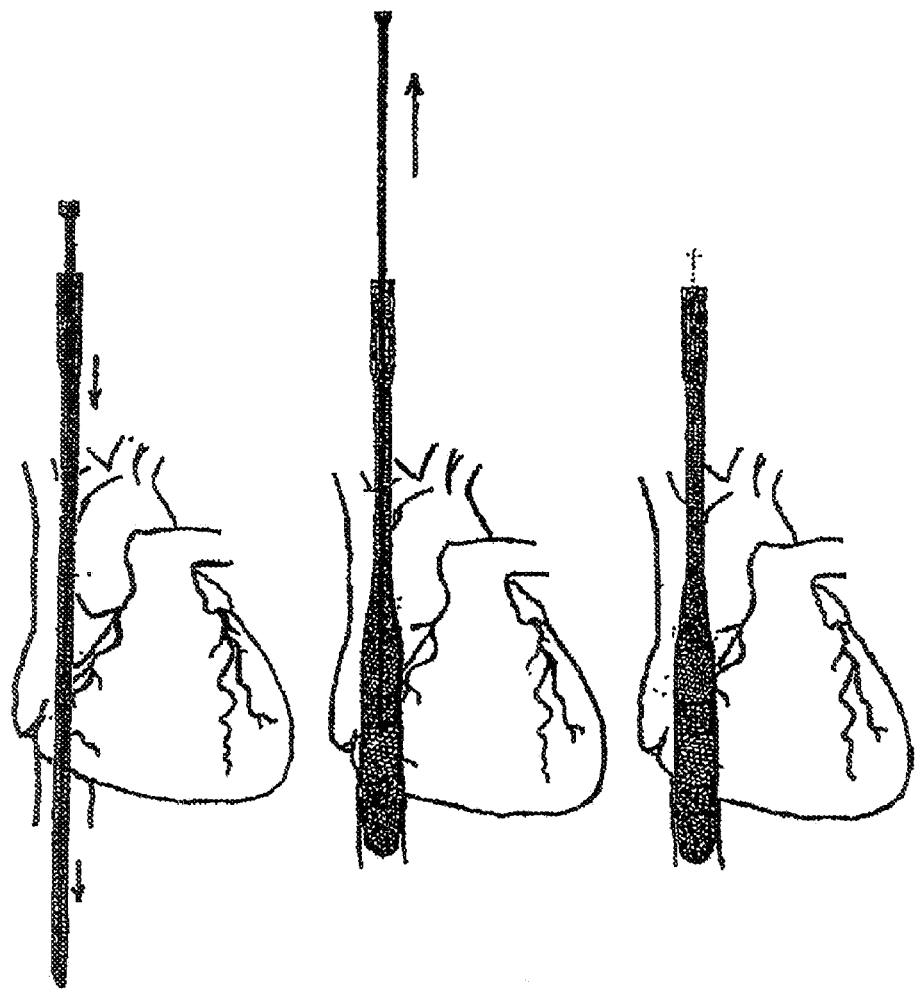
FIGS. 1-3 show a mechanism of deployment of a dual-stage venous dynamic cannula into the anatomical position.

Definitions:

For the purposes of the present disclosure, the following terms shall have the associated meanings. Reference in any given embodiment to a term defined below is to be understood as incorporating the broadest definition of such term.

The term "cannula" shall mean a tube which can be permeable, impermeable, partially permeable, partially impermeable, or selectively permeable to fluid.

The term "stent" shall mean a structure that can support an anatomical structure, such as, but not limited to, a blood vessel, intestine or other structure, by exerting a force counter to a collapsing or shrinking force exerted by the anatomical structure.

The term "conduit" shall mean a fluid impermeable tube capable of conducting a fluid from a first location to a second location.

The term "wire structure" shall mean a structure that is formed from a plurality of filaments, segments or pieces of material into a mesh, woven, nonwoven, overlapping, interlacing, braid, lattice, web, net, interlocking, knit, combinations or mixtures of the foregoing or other structure. The wire can have any regular or irregular cross-sectional shape, such as, but not limited to, circular, oval, elliptical, flat, rectangular, or the like. The term "wire structure" is also defined to include overlapping plates or segments of material, such as, but not limited to, a "chain mail" armor or armadillo-skin armor-like structure. The term "wire structure" is also meant to broadly include a structure that can be inserted into a hollow tube-like structure and at least a portion of which expand from a first diameter to a second diameter.

DETAILED DESCRIPTION OF THE EMBODIMENTS

Dynamic Radius Cannula

In a cannula according to a first embodiment of the present invention, reversible radial expansion and contraction memory properties were conferred by using a wire structure. The shape memory may be due to the material, the configuration, or a combination of both material properties and the configuration. In other configurations, a combination of materials with different properties may provide the desirable characteristics. For example, but not by way of limitation, a wire mesh can provide radial memory and a silicone covering can dictate the final expanded diameter and the rate or force of expansion.

Suitable materials for cannulae of the present invention include, but are not limited to, substances biologically inert and capable of forming a structure or with some degree of shape memory properties. A wide range of materials including, but not limited to, metals, such as, but not limited to stainless steel and silver, nitinol, plastics, monofilament or multifilament polymer, shape memory polymers, silicones, fluorocarbons, glass, acrylics, ceramics, impregnated ceramics, or biological tissues or the like and/or mixtures, combinations, alloys or composites thereof, may be suitable. One preferred such substance used to construct a prototype cannula of the present invention is commercially available under the trade name WALLSTENT™ from Boston Scientific, Inc., Natick, Mass. Other brands and types of material can be used to form the cannula. It is also possible to form the wire structure out of two or more distinct materials that are interwoven.

Where the material is wire mesh, the wire can have a cross-sectional shape, such as, but not limited to, circular, oval, elliptical, polygonal, curved, stepped, or other regular or irregular cross-sectional shape or geometry. A smooth shape is preferable to minimize trauma to the blood vessel and reduce fluid flow resistance.

Configuration

As noted above the configuration of the material can be segments of wire or wire-like or threadlike material and can be interwoven, interlocking or otherwise connected in a flexible manner to permit expansion and contraction of the diameter. The structure can also be described functionally as being provided in a tubular or funnel shape. Alternatively, the mesh can be made of polymeric material molded into a mesh. In other configurations, the elastic properties of the material itself may confer the shape memory. Alternatively, the material may fold upon itself in a longitudinal plane to radially contract and unfold to radially expand. The material of the cannula can also be made of an elastic material. It is also possible that the structure is multilayered.

The wire structure can optionally have a biologically inert fluid-tight covering or coating, such as, but not limited to, silicone, polyurethane, PTFE (polytetrafluoroethylene), mixtures thereof or the like along at least a portion of the mesh. Alternatively, the coating can be selectively or partially permeable. It is possible for the coating to act as a filter for certain materials. Moreover, the coating can be chosen to be able to selectively adsorb or absorb certain materials present in body fluid or the fluid in which the cannula is introduced. Additionally, at least a portion of the structure can be coated on the inside wall with a first material and coated on the outside wall with a second material. The first and second materials can be the same or different. The wire structure, porous or not, can be impregnated or coated with a therapeutic or other bioactive agent, for example, but not by way of limitation, antithrombus, anticoagulant, hemostatin (where clotting is desired), heparin-like material, mixtures thereof or the like. It is possible that the wire structure call be a biodegradable polymer such that the cannula is left in the patient and is eventually degraded or absorbed.

The wire structure or the covering may act as a selective filter. Artherosclerotic particulate matter dislodged from the blood vessel wall during manipulation is one possible material to filter or capture. The filter could act to separate particulate matter in the stream of blood vessel flow or within the cannula itself. The cannula coating may be "sticky" for particulate matter. The coating or impregnated substance can be radio opaque, translucent or transparent. The coating can be radioactive, such as with beta radiation.

At least a portion of the diameter of the cannula can be reduced from a first diameter to a second diameter by imposing a longitudinal extension force on the material which can elongate the material. Alternatively, a radial compression force can be applied by an external sheath or ring to constrict the diameter. Alternatively, a mixture of axial and radial force (e.g., twisting) can be applied.

In one embodiment a distal end of the cannula has an end portion or cap associated therewith. When longitudinal extension force is applied to the distal end proximally, the diameter contracts in the radial direction. Relieving the force results in radial expansion. Alternatively, if a longitudinal contraction force is applied to the ends of the cannula, the stent expands in the radial direction. The longitudinal extension force can be a rod, trocar or guidewire that is inserted into the proximal end of the cannula and extended to the distal end. As the rod contacts and pushes the cap, the wire mesh elongates and the diameter is reduced or collapsed (FIGS. 1-3). By "collapsed" it is meant that at least a portion of the cannula has a diameter that is reduced from its expanded diameter. In certain cases, it may be advantageous for the cannula diameter to contract only part way.

The end portion or cap can also have a central orifice to allow passage of a guidewire. The end portion can be fluid permeable to permit fluid flow therethrough. The end portion can be constructed as a grid, mesh, net, ring or other framework of material or can be solid or open.

The wire structure can also be electrically actuable such that the cannula diameter expands or contracts in response to an electrical signal. The signal can be a passive or active signal from a control source located internal or external to the patient and can be wireless or connected to the cannula by a wire. The wire structure can also be thermally actuable such that the structure expands or contracts in response to a change in temperature, such as that from ex vivo to in vivo.

One advantage of the embodiments of the present invention described above is that insertion of the cannula of the present invention may be less traumatic to vessel than conventional cannulae, since the cannula's outer diameter (when released) can be appreciably less than the blood vessel's inner diameter during insertion. Since at least a portion of the cannula diameter expands after insertion, the radially expanding outer diameter of the cannula potentially "custom-fits" to the inner diameter of the blood vessel, and is capable of expanding to the largest possible diameter that fits in a given vessel. When the vessel has a changing diameter over a given length the cannula of the present invention can expand to various diameters along the cannula length to form fit a given length of vessel. In addition to the fluid dynamics advantages of a larger diameter cannula, the expandable cannula can fit firmly against the vessel's inner wall, preventing fluid leakage around the cannula. After deployment the cannula potentially contours to the surgically unexposed inner diameter of the blood vessel. This property may improve the function of cannulae in irregularly shaped vasculature and during minimally invasive surgeries characterized by limited visual exposure of the patient's anatomy.

Withdrawal of the cannula is potentially less traumatic to vessels since the expandable material may be contracted back down to a smaller diameter prior to withdrawal. This may be accomplished by the nature of the expandable material. When the cannula material is externally compressed, it contracts its diameter a distance from a site of constriction along its length. Alternatively, a trocar may be reinserted as an actuator to force elongation and reduce the diameter of the expandable portion of the cannula prior to withdrawal. Another useful method for this purpose may be drawing the cannula back through an external sheath or ring or advancing a sheath or ring along the cannula to narrow its diameter.

Figure 4:
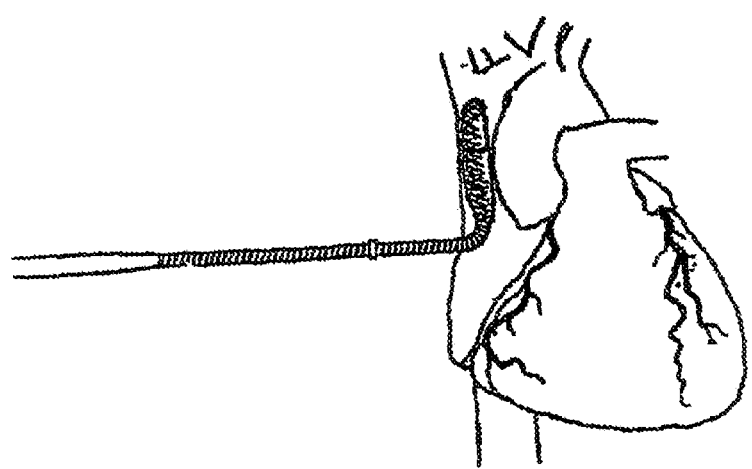
FIG. 4 shows a single-stage venous cannula according to one embodiment of the present invention.
Figure 5:
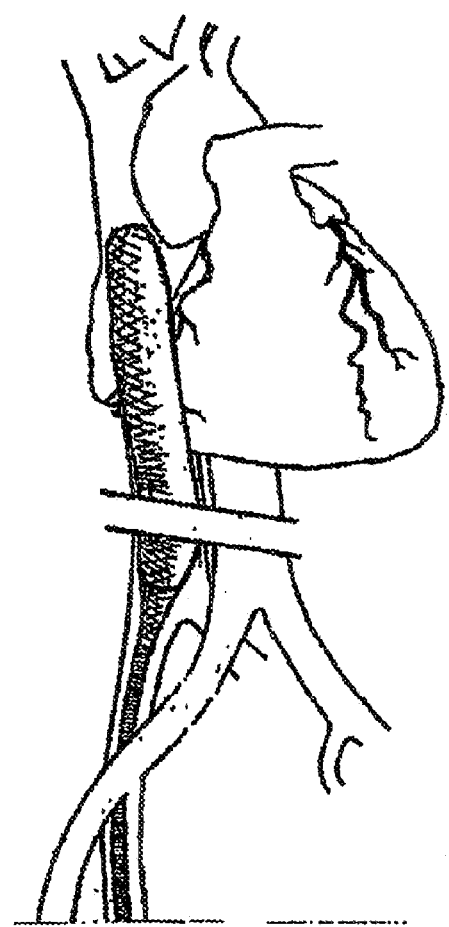
FIG. 5 shows a femoral venous cannula according to one embodiment of the present invention deployed into the anatomical position.
Figure 6:
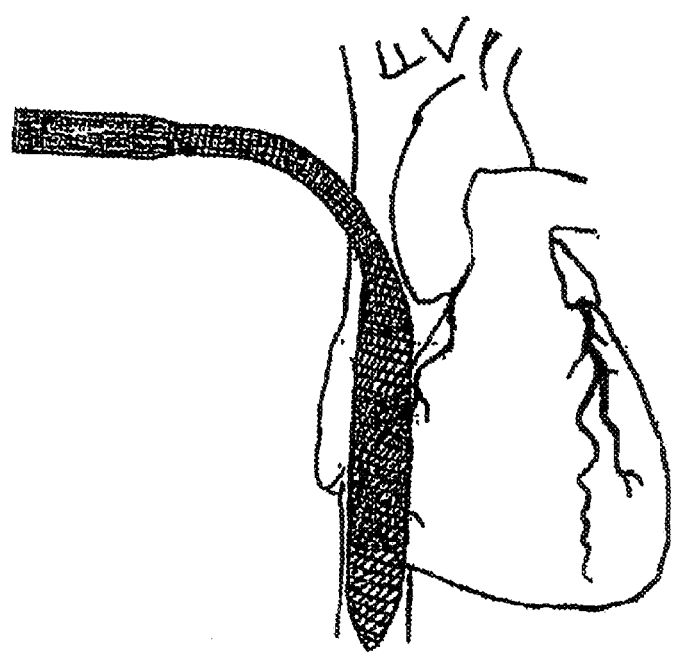
FIG. 6 shows a dual-stage venous drainage cannula according to one embodiment of the present invention.

After deployment, the radial expansion of the cannula may exert a force on the vessel wall that acts to stent it open. In venous applications, this property may help to decrease vessel collapse, particularly during vacuum-assisted drainage (see FIGS. 4-5). FIG. 6 shows a venous application embodiment of a venous femoral cannula The radial expansion property of the specialized cannula tip potentially eliminates the user having to select the size of the cannula for each procedure. One size cannula fits many size blood vessels, which may potentially increase availability, while decreasing cannulae product inventory.

The "custom-fitting" nature of the cannula and the force it exerts on the vessel inner wall may help secure the cannula in place. This may eliminate the need for sutures in certain applications.

Funnel Shape

Figure 7:
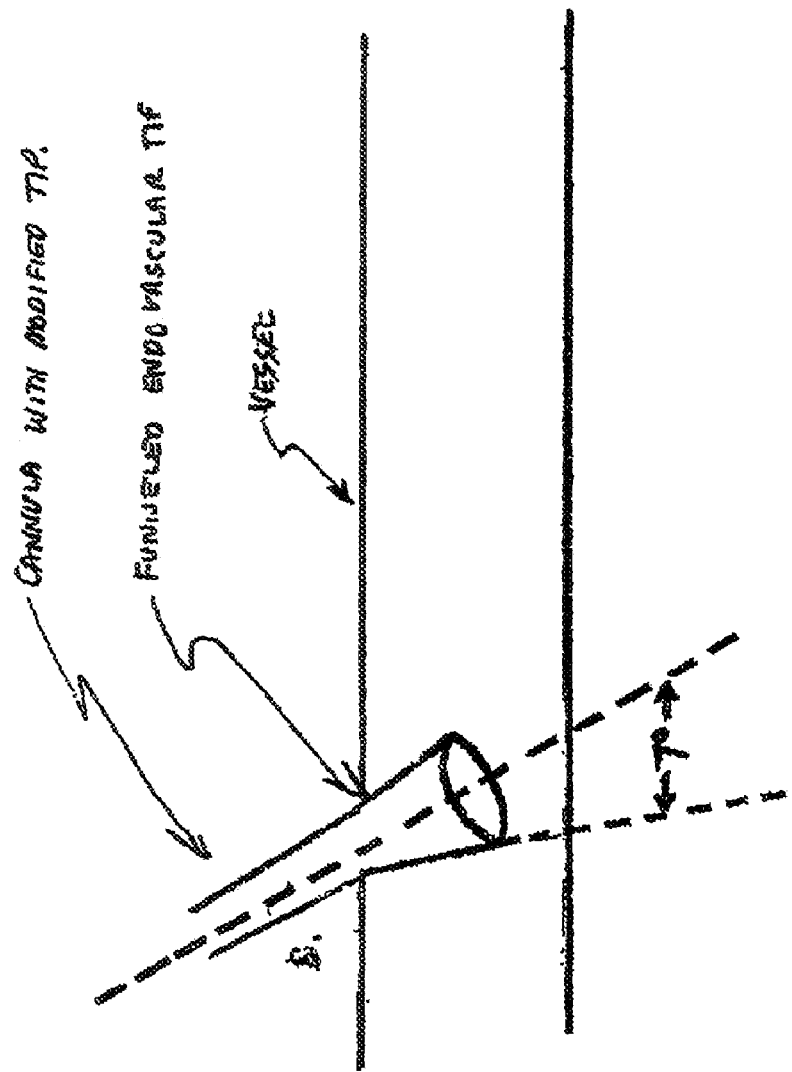
FIG. 7 shows one embodiment of the present invention depicting a cannula with a funneled endovascular tip positioned in a blood vessel.
Figure 8:
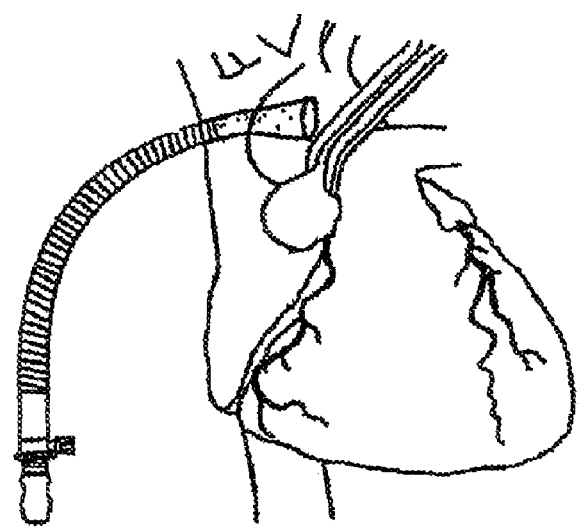
FIG. 8 shows a cannula according to one embodiment of the present invention depicting anatomical position during aortic cannula usage for cardiopulmonary bypass.

According to a second embodiment of the present invention, as shown in FIGS. 7-8, a cannula can contain a portion that forms a funnel or flared shape to ease the transition in cross-sectional area size discrepancies between the extracorporeal line, the cannula, and the blood vessel. By "funnel" it is meant that at least a portion of the cannula has an increasing or flared diameter. Such funnel area can be proximate to either end or somewhere between the two ends of the cannula. The flared portion can be angular (i.e., straight) of curved, either convex or concave, grooved, ribbed or the like as the situation warrants. The shape memory properties of the stent material used in the cannula construction can be used to create a pre-determined funnel shape and angle or curvature. In one embodiment it was found that a 7 degree angle demonstrated a decrease in pressure drop across a range of fluid flow compared to its standard cannula counterpart. The angle depends on a variety of parameters, such as, but not limited to, velocity, viscosity, diameter and length of the tube. Depending on these parameters, an angle of up to about 20 degrees, or even possibly more, can be used.

Figure 9:
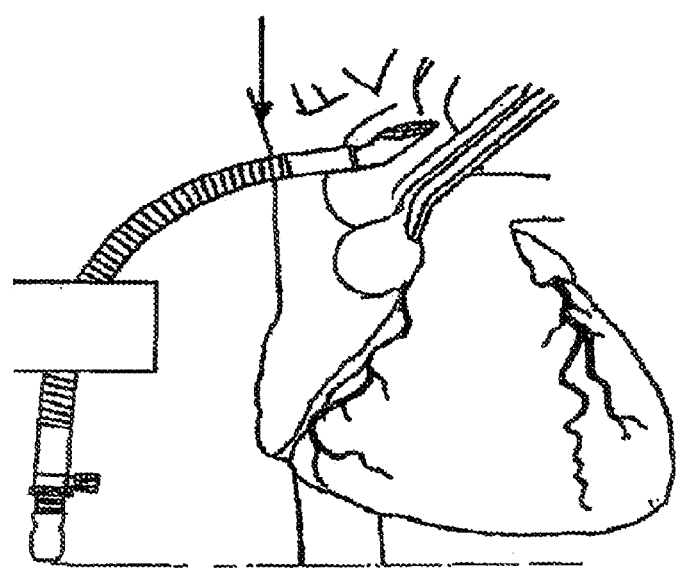
FIG. 9 shows a cannula according to one embodiment of the present invention depicting a funneled, curved-tip, mesh enclosed-end aortic cannula usage during cardiopulmonary bypass.
Figure 10:
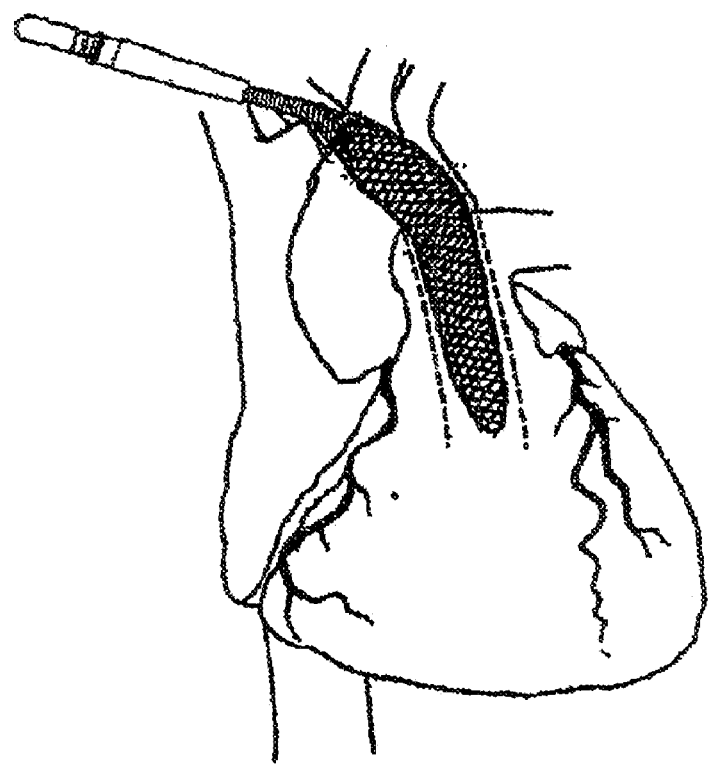
FIG. 10 shows a descending aortic dynamic cannula according to one embodiment of the present invention.

One method of deployment can be a mechanism, shown in FIG. 9 having an open distal end with a mesh or lattice structure over the distal opening and capable of receiving a force, such as from a trocar to reduce the cannula radius. FIG. 10 shows an embodiment insertable into the distant site of the descending aorta.

One advantage of the funneling of the cannula of this embodiment is to improve the fluid dynamics of diameter size transitions between the cannula, the blood vessel, and the extracorporeal equipment.

Occlusion Cannula

In a third embodiment of the present invention a cannula is provided that can occlude fluid flow. During surgical procedures, the blood flow within a vessel is commonly controlled by a specialized clamp that compresses the vessel. It is a drawback that the clamp may traumatize the vessel, mobilize embolic particles, or obtrude into the surgical field. In an attempt to overcome these problems, internal occlusion of blood vessels using a gas or fluid-filled balloon has been made commercially available for certain applications.

A cannula according to this embodiment can act to control blood flow through a vessel by contracting or expanding its radial diameter. Fully expanded, the device can enlarge to exert a radial force on the inner wall of the vessel such that fluid is unable to longitudinally pass around the outer diameter of the device. Alternatively, the mechanism for expanding the cannula diameter may be elicited by a longitudinal force. In the prototype, a longitudinal compression force exerted on the cannula acts to expand its radial diameter. This actuator may be a pulling force, as with, for example, but not limited to, a guidewire attached to the distal end and pulled proximally. The actuator may also be, but not limited to, a pushing force, such as a fluid exerting a radial force on the cannula wall.

An advantage of this embodiment is the ability of an occlusion cannula to control blood flow through changes in radial diameter may be a less traumatic means of controlling blood flow. The atraumatic nature of the cannula may be conferred by its ability to function inside the vessel and reduce or eliminate distortion on the vessel's native geometry during control of blood flow. It may also be less traumatic that the cannula has the ability to be radially expanded or contracted in a graded fashion under a controlled means (for example, guidewire or fluid exerting force on cannula) to suit the requirements of the procedure or the size of the particular vessel.

Filtration Cannula

In a fourth embodiment of the present invention a cannula is provided which can act as a particle filter. The cannula of this embodiment may have a mesh structure (e.g., WALLSTENT® material) which can function to selectively filter particles in the stream of fluid flow. In one such configuration, a prototype cannula was constructed that functions to entrap and capture downstream particles in the distal tip of the cannula.

Providing a filtration function to a cannula according to this embodiment with a dynamic radius may permit more selective and efficient filtering of particles in blood vessels. The ability of such a cannula to change diameter may offer an advantage in filtering, effectiveness given the variations in inner diameter both within and between various blood vessels.

Thin-walled Cannula

In a fifth embodiment of the present invention a cannula may be constructed from materials that reduce the cannula wall thickness (the difference between the cannula outer and inner diameter). The strength of the wire reinforcement of the covered material used in such a cannula permits ultra-thin wall construction.

An advantage of this embodiment is that such a cannula eliminates the "step-off" created by the wall thickness of standard cannulae, thus improving fluid dynamics. Additionally, such a cannula can improve fluid flow by maximizing the inner diameter. Such a cannula can stabilize cannula placement in the blood vessel since fluid flow has no "step-off" in the stream of flow upon which to exert a displacement force.

Close-ended Cannula

Figures 13A, 13B:
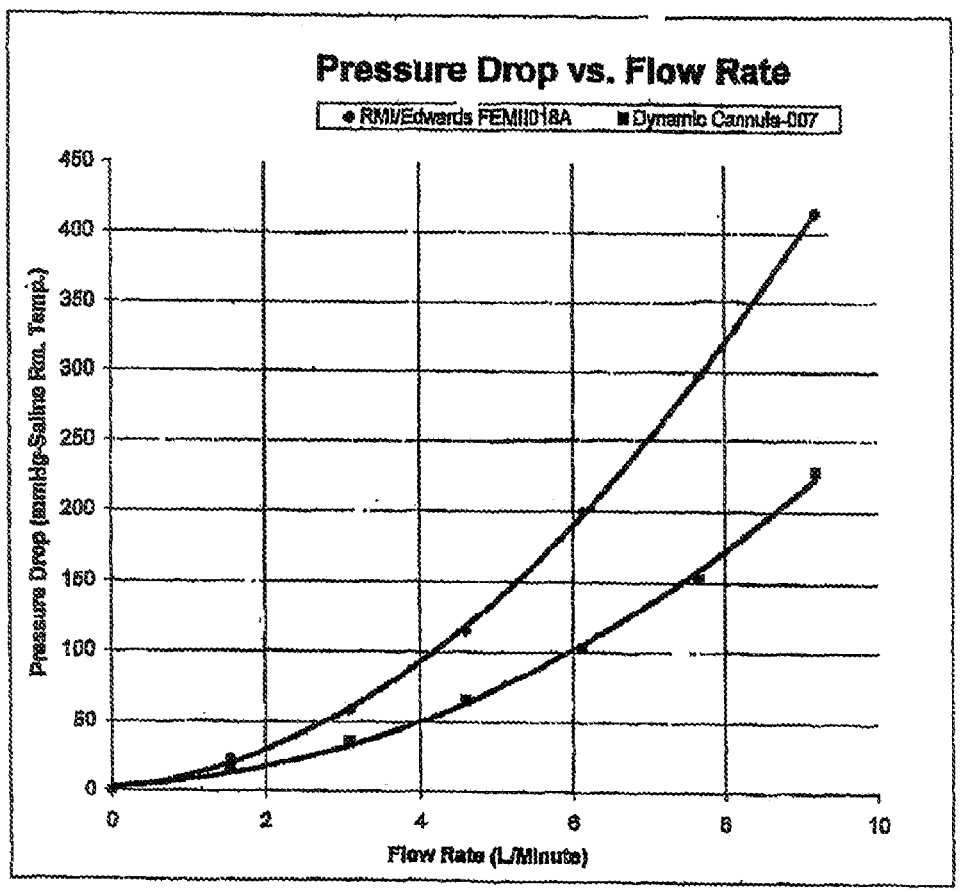
FIG. 13A, B shows a graph of pressure drop vs. flow rate and a specification table in a dynamic femoral arterial cannula vs. standard industrial counterpart.

In a sixth embodiment of the present invention a cannula can he configured in an open-ended or close-ended configuration. FIG. 11A shows a conventional close ended cannula. FIG. 11B shows a conventional trocar. FIG. 12A shows a closed ended cannula of the present invention and FIG. 12B also shows a conventional trocar. In such a cannula, the ends are closed by associating the wires of the structure together at the distal end, such as, but not limited to, by joining, adhering, gluing, compressing, fusing, twisting, braiding or the like. A small orifice optionally can be maintained at the closed-end to allow passage of a guide wire. FIG. 13A shows a graph of the pressure drop versus flow rate and FIG. 13B shows a specification table of an illustrative cannula of this embodiment.

An advantage of this embodiment is that a close-ended configuration offers a site for a trocar inserted within the cannula to exert a longitudinal force on the stent. This enables the cannula to convert reversibly from a constricted state to an unconstricted (radially expanded) state by trocar removal without traumatizing the blood vessel or surrounding tissues. The mesh formed in the stream of flow by closed-end of the wire stent configuration may act to diffuse force exerted by fluid flow and increase laminar flow. Moreover, the bluntness of the close-ended design may be less traumatic to the vessel wall.

Selective Portion Control

In a seventh embodiment of the present invention a cannula is provided with selective portions containing expandable and contractable segments.

In an eighth embodiment of the present invention a cannula is provided that is capable of three planes of change and all permeations and combinations of these planes and subcategories; i.e., radial plane (expanded or contracted); longitudinal plane (elongated or shortened); and, circumferential plane (clockwise torque, counter-clockwise torque or no torque).

Proximal Funneling

The cannula of the present invention possesses the property of being able to assume a funneled or tapered configuration to improve the dynamics of fluid or gas passage through an area of constriction or expansion in its path (FIG. 7). A potential constriction in the fluid path is the narrowed portion of the cannula as it passes into the vessel, tissue, space or potential space being cannulated. An example of possible rapid expansion in the fluid path is the exiting of blood from an 8 mm internal diameter cannula into a 30 mm endovascular space of the ascending aorta during aortic perfusion in cardiopulmonary bypass.

Figure 14:
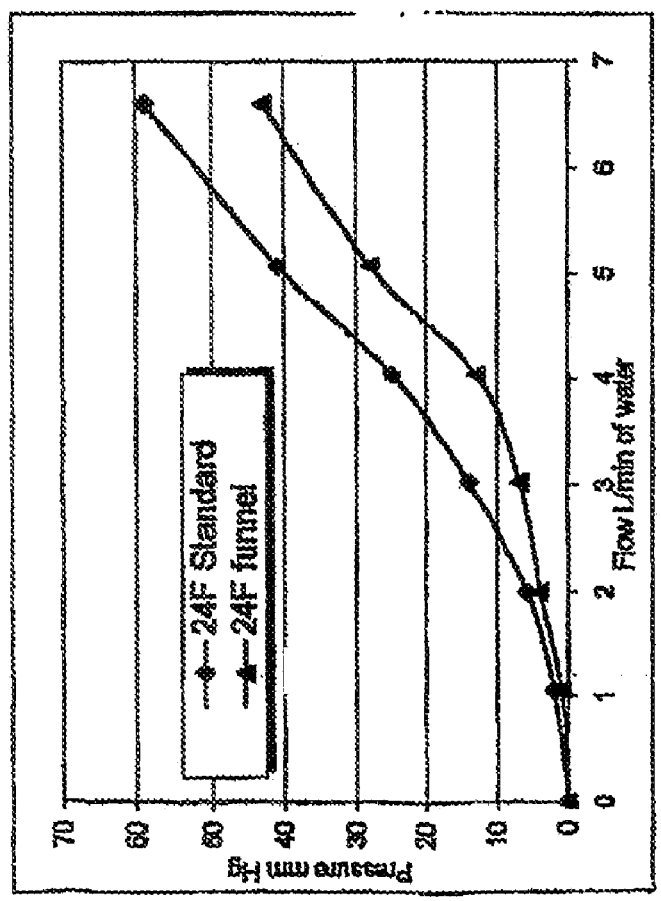
FIG. 14 shows a graph of the pressure drop versus fluid flow (water) through the cannula according to the embodiment shown in FIG. 1b compared to its standard industry non expendable cannula counterpart.

In our laboratory studies of aortic cannula, replacing the tip of a 24 French cannula with a funneled structure (7 degree angle from center axis) of identical length ("modified tip"), resulted in a significant decrease in pressure loss across a range of flows as compared to the standard straight tip cannula (FIG. 14). A visual display of turbulence testing demonstrated a potentially less turbulent jetstream exiting the funneled-tip cannula versus the straight-tip cannula. In a laboratory test, the area of cannula spray was greater and exit force velocity was significantly less for the funneled "dynamic" cannula prototype than the non-funneled 24 French cannula.

Distal Funneling

Figure 15:
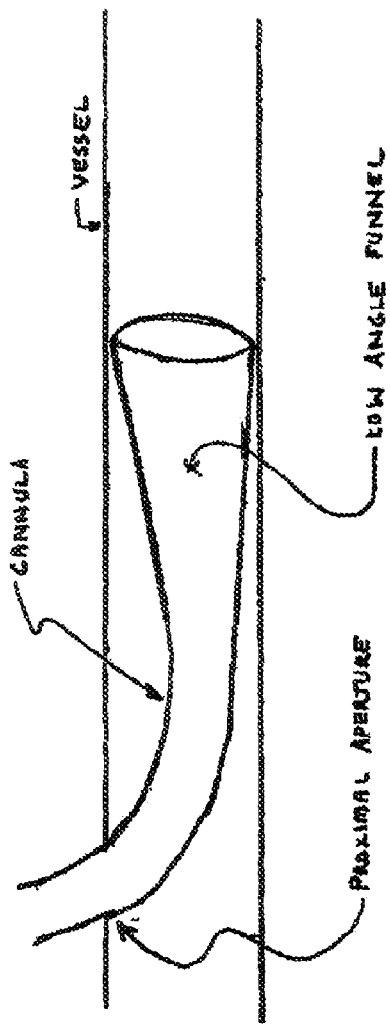
FIG. 15 shows a cannula gradually funneling from proximal aperture.
Figure 16:
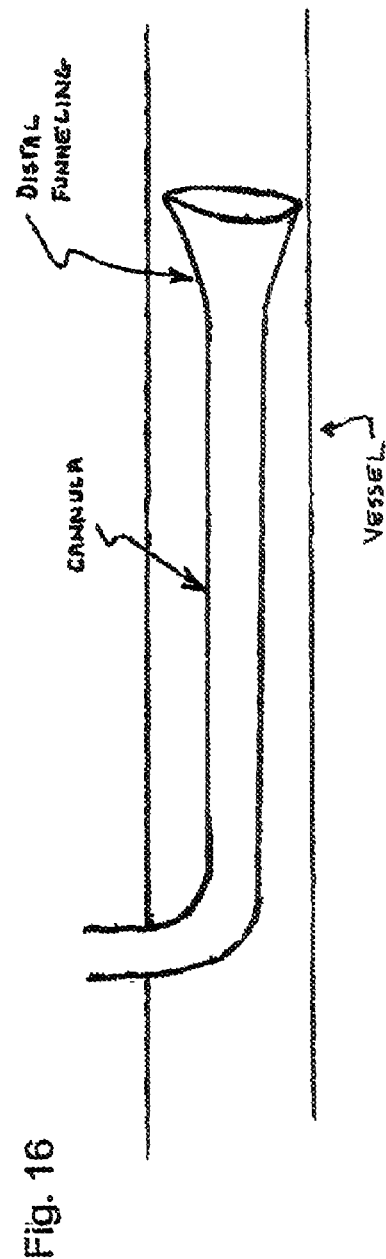
FIG. 16 shows the distal funneling.
Figure 17:
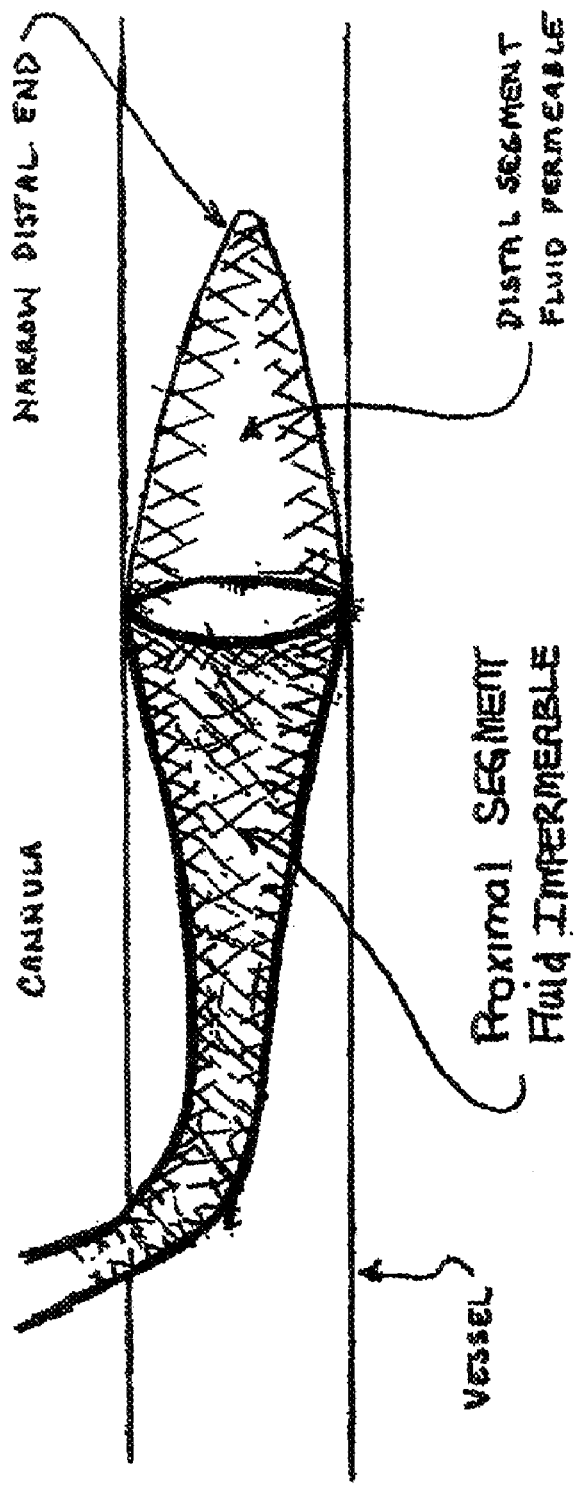
FIG. 17 shows the cannula funneling to narrow point, distally.
Figure 18:
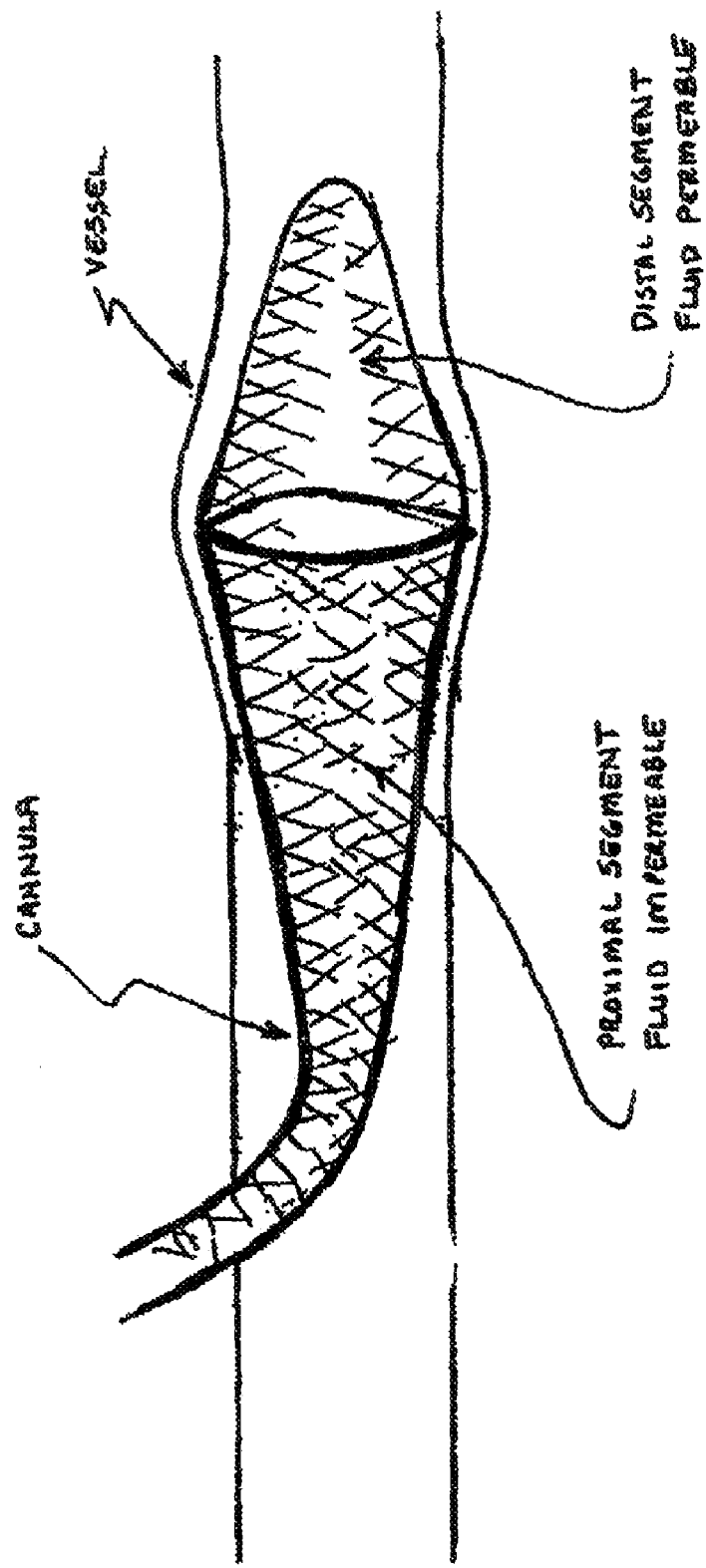
FIG. 18 shows the cannula exerting radial force on vessel.

The present invention provides an eighth embodiment and a cannula which may also be funneled at a distal site (see FIGS. 15-17). For example in the configuration of an expandable venous cannula, the distal end is the site of entry of venous return into the cannula. This site can be funneled to increase the laminar flow and reduce the pressure drop which can increase or cause collapse of the compliant vessel distal to the cannula. There are various configurations of distal funneling. These include funneling gradually from the aperture diameter (FIG. 15) or funneling from a more distal point (FIG. 16) to a larger diameter distally. The funneling may also be a tapering to a more narrow point distally (FIG. 17). The funneling may also exert a radial force, expanding the vessel it cannulates (FIG. 18). Note that in this configuration, the cannula includes both a uncovered (non fluid-tight) and covered (fluid-tight) portions of the structure.

Distal funneling may reduce chattering (i.e., collapsing vessel) which occurs at a point where the coated (i.e., liquid impermeable) area of the cannula changes to a partially coated or uncoated area. As shown in FIG. 7b the cannula at its widest point expands beyond the native state diameter of that area of the blood vessel in which it is indwelling.

Double-layered Cannula

Figure 19:
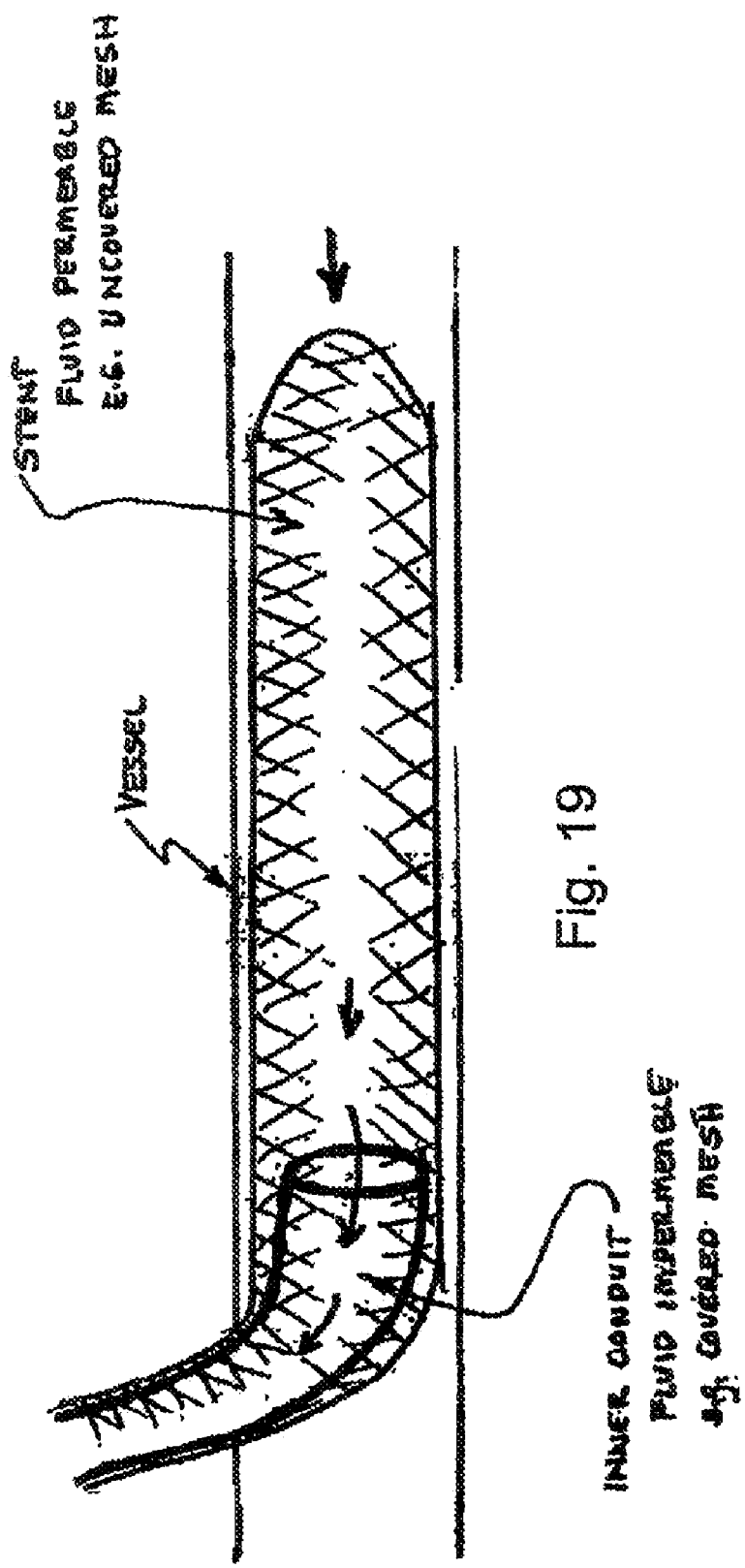
FIG. 19 shows the double cannula with inner conduit and outer stent.
Figure 20:
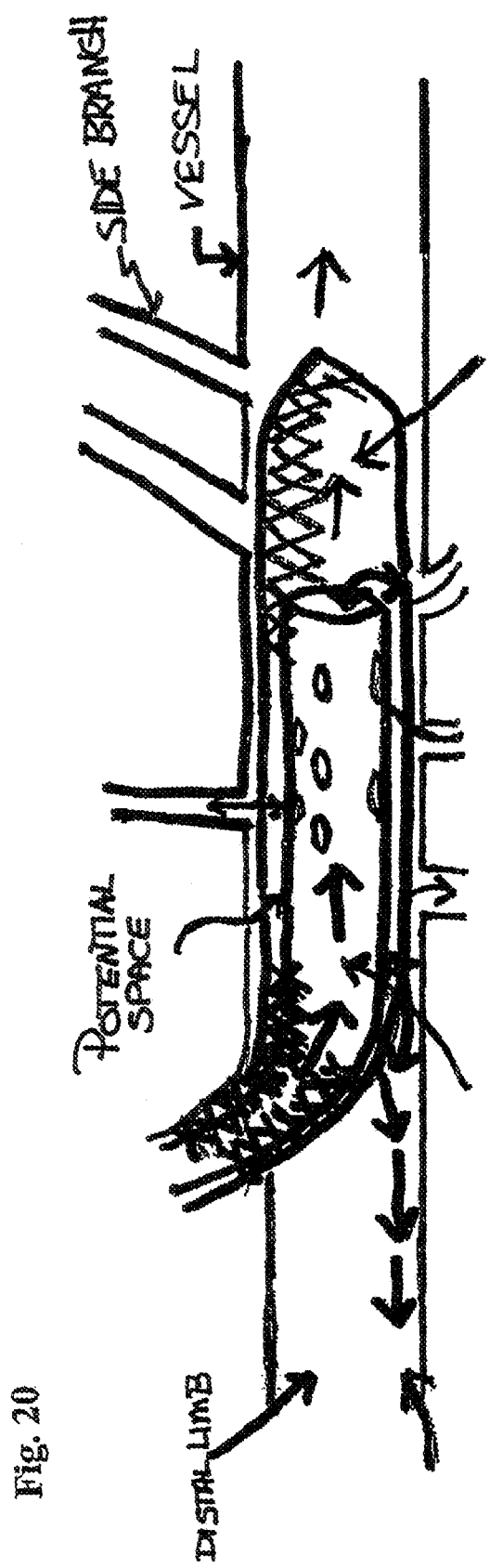
FIG. 20 shows the cannula in double configuration in vessel with side branches.

In a ninth embodiment of the present invention, shown in FIGS. 19-20, a cannula can be constricted as a double-layered (also referred to as co-axial or dual lumen) structure, comprising both fluid permeable and fluid impermeable portions.

Figure 21:
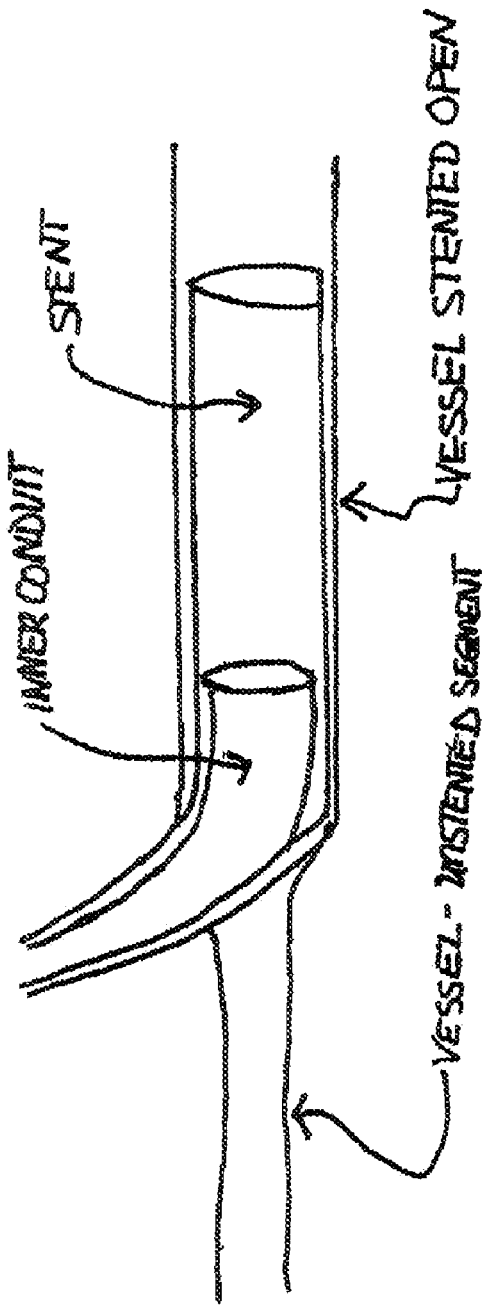
FIG. 21 shows the cannula acting to stent vessel proximally.
Figure 22:
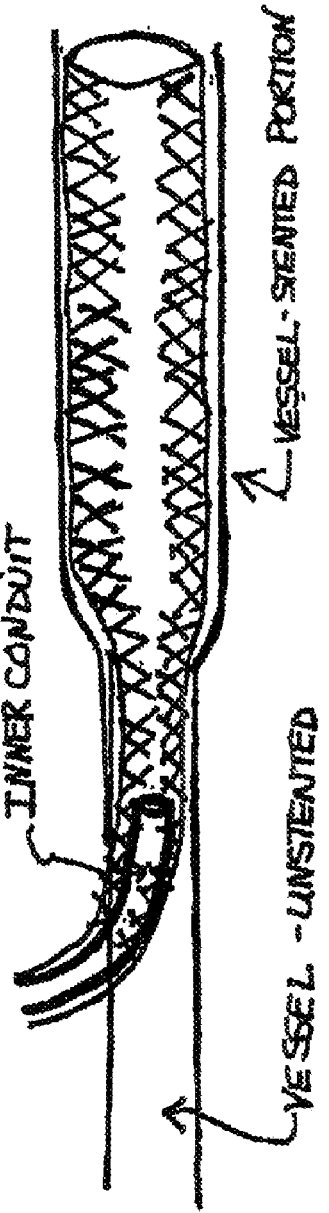
FIG. 22 shows the cannula stenting vessel distally.

One such structure, shown in FIG. 19, is a cannula consisting of a combination of an outer wall of non fluid-tight layer (e.g., outer uncovered stent or mesh or other material as described hereinabove) and an inner wall fluid-tight conduit. In this configuration, the cannula has a proximal end, a distal end, and a lumen between both ends. The diameter of the stent and the conduit can be varied together or indepedently. Both the stent and the inner conduit diameter can be varied to account for the differences in the internal diameter of the structure into which the cannula is inserted. When placed inside a structure, such as a blood vessel, the outermost stent functions to expand or prevent collapse, limit the degree of collapse, increase rigidity, or protect the wall of the structure it cannulates. The outermost stent can also function to create a potential space for fluid passage between vessel sidebranches and the innermost conduit (see, FIG. 20). The outermost stent can function in conjunction with the structure to provide a conduit for fluid or gas. The cannula can exert a radial force to expand the cannulated structure at various proximal or distal sites along the fluid path (see, FIGS. 21-22).

The innermost and outermost layers can be purposefully positioned and changed relative to one another before, during, or after cannulation or deployment. The inner conduit structure functions as a passageway for fluid or gas, providing a non-leaking pathway in and out of the cannulated structure and the body. The outer most layer functions to "stent" the vessel, allowing the vessel to act as its own conduit. When used in combination with the outer stent, the inner conduit acts to provide a fluid-tight passageway for fluid into and out of the body and can be significantly shortened in length compared to traditional cannula. Shortening the cannula would decrease the resistance in cannula and confer a potential improvement in the fluid dynamics.

Figure 23:
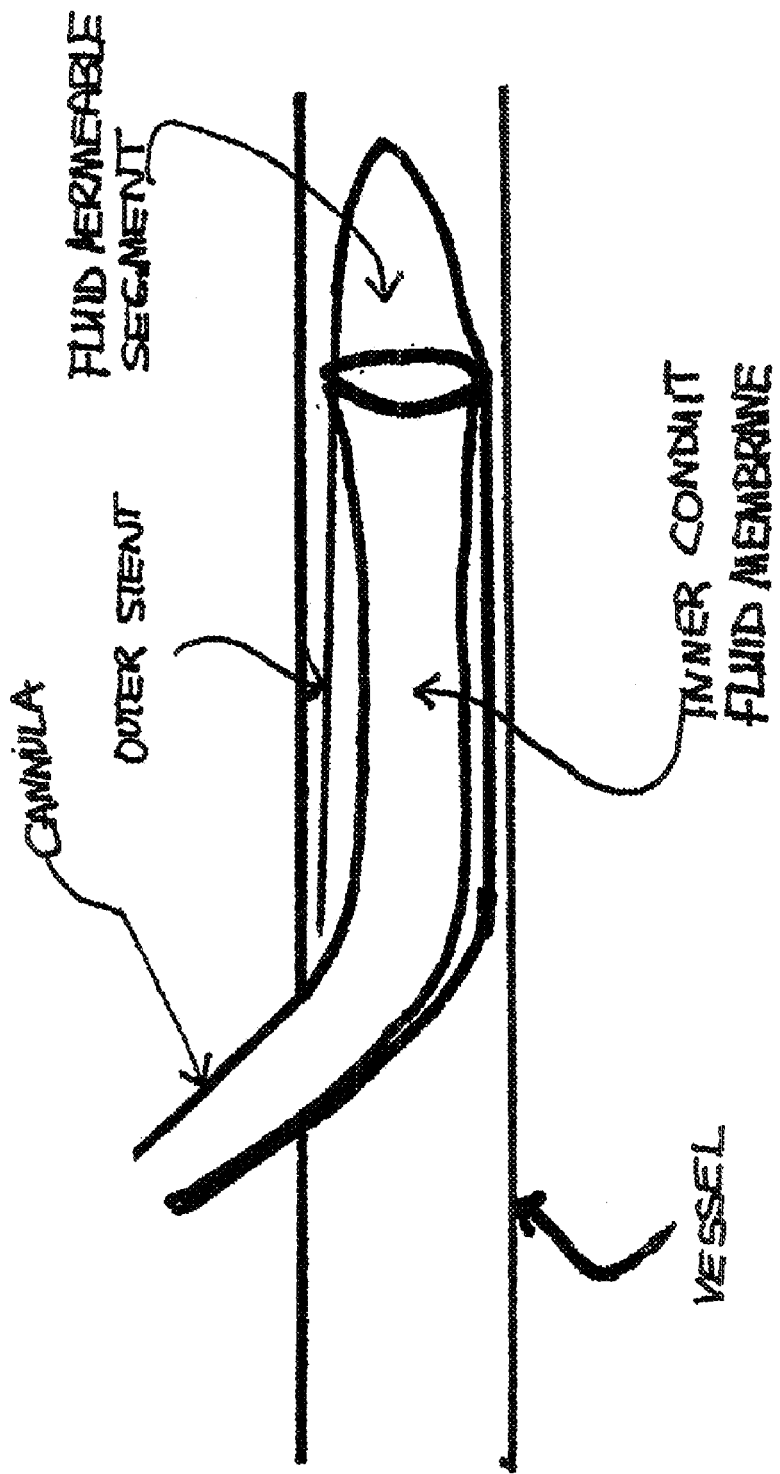
FIG. 23 shows the cannula with inner conduit funneling.

The cannula is characterized by providing a small entry orifice or aperture into the cannulated structure. The inner conduit or the outermost stent can be funneled or tapered to improve fluid dynamics (FIG. 23). The outer wall and inner wall of the conduit can be single-ply or multi-ply. The outer and inner walls can be interlaced or interwoven. The outer most layer can also be a fluid-tight (i.e., impermeable), partially permeable, or wholly permeable material. If both inner and outer layers are fluid impermeable, the cannula can be deployed in a completely open configuration as described below.

Open-ended Deployment

Figure 26:
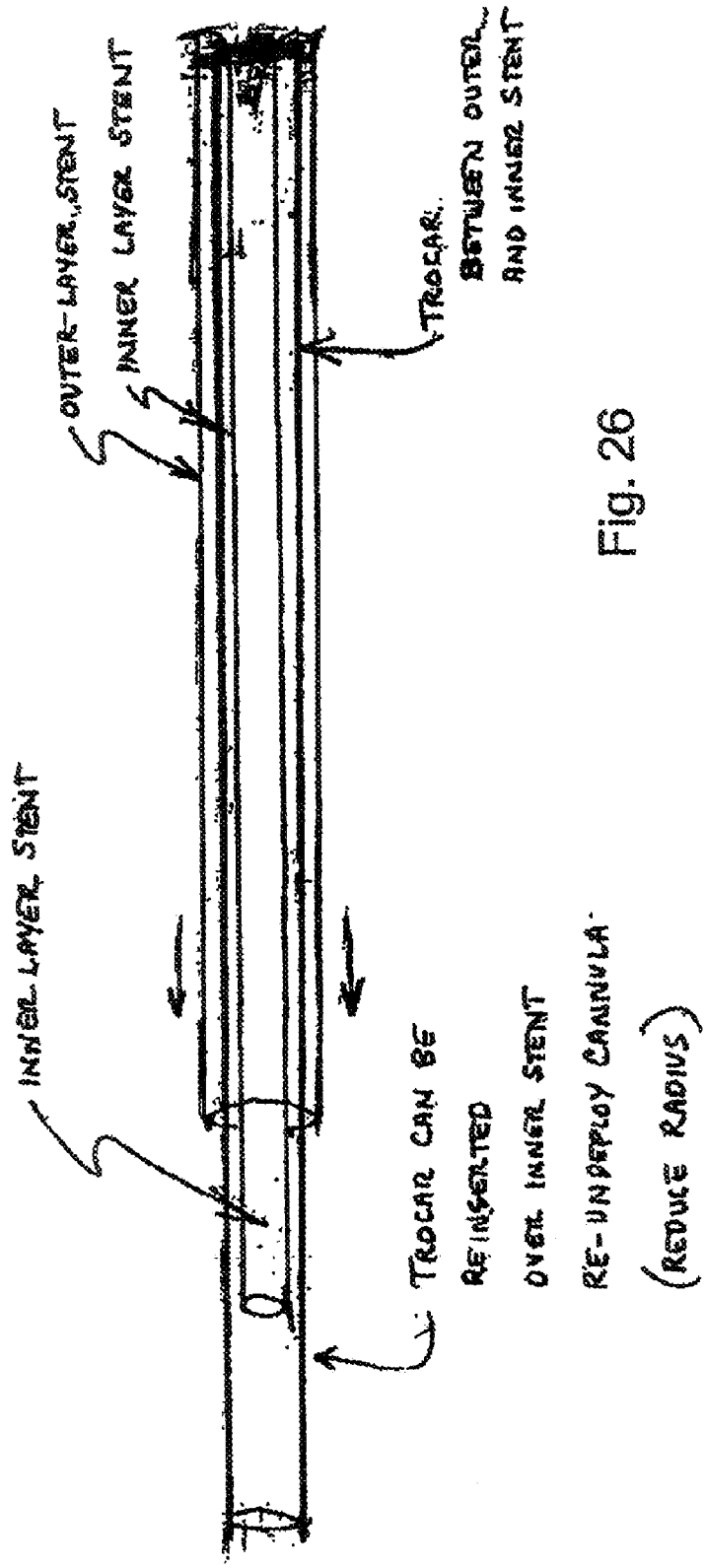
FIG. 26 shows the double layer cannula with long inner layer stent.

In a tenth embodiment of the present invention, an open-ended cannula is provided, shown in FIGS. 24-26, whereby in one such configuration, the double layer of inner and outer expandable material provides a surface for an opposing force to elongate the cannula and reduce its diameter. In one design, a tubular trocar positioned between the inner-most layer and outer-most layer of the cannula exerts a longitudinal force on the distal end of the cannula relative to the proximal end (FIG. 24). The longitudinal force elongates the cannula and narrows its profile. When the trocar is removed, the cannula is free to radially expand both layers into a completely open-ended structure (FIG. 25). This allows the cannula to deploy into the fully open-ended configuration without any obstruction in the fluid path. It also permits other instruments to be passed through the completely open-ended cannula. An advantage of this mechanism is that it constrains the cannula in the narrow diameter using an inner trocar without the necessity of an external sheath as described by others. This eliminates the familiar problem of having to withdraw or peel back a sheath ("break-away sheath") back over larger diameter inner segments as encountered in placing tunneled indwelling subcutaneous access lines.

In a variation of this embodiment, shown in FIG. 26, the structure is designed with the inner layer stent proximal end being longer and extending beyond the outer layer stent to allow the trocar to be reinserted over the inner layer and inside the outer layer in the cannula while it is in the deployed position. This would enable the diameter of the cannula to be narrowed prior to removal from the cannulated structure. The cannula can alternatively be removed from the trocar and deployed by pushing an inner rod into the trocar, effectively pushing the cannula out of the trocar. The ability to reduce the diameter of the cannula can be useful for repositioning the cannula following deployment.

Pulling vs. Pushing Mechanism of Cannula Deployment

As previously described, one mechanism of cannula deployment is to "push" the cannula in place then withdraw an inner trocar or guidewire thereby releasing the elongation force on the distal part of the cannula. The cannula is then free to radially expand and shorten its length. In certain applications it may be problematic that the exact location of the distal tip of the cannula is unknown following shortening. In certain uses it may be that the cannula may need to be advanced beyond the final desired position in order for it to assume the correct position with the cannulated structure.

Figure 29:
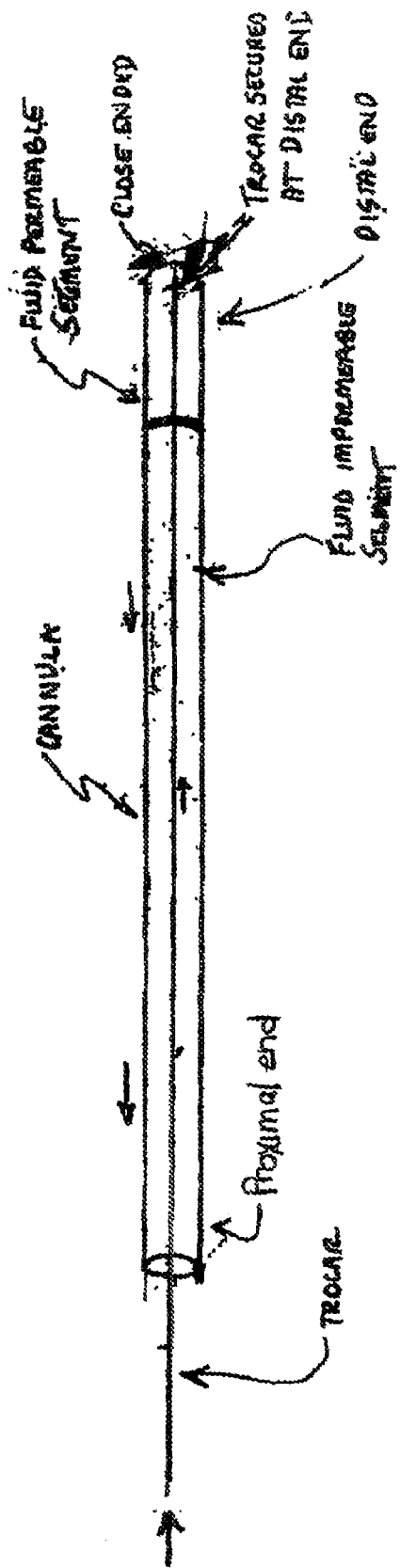
FIG. 29 shows a cannula with a centered guidewire attached to the distal tip.

In an eleventh embodiment of the present invention, shown in FIGS. 27-28, the deployment trocar is an integral part of attached permanently or removably to the distal portion of the cannula. In this embodiment, the trocar is advanced during cannulation with the cannula into the vessel. The cannula, which is temporarily attached (such as by friction fit) proximate to the proximal end, is released at its proximal attachment site such that the cannula advances into position by moving forward relative to the trocar (FIG. 28). The trocar can be positioned off-center as shown in FIG. 28 or centered as shown in FIG. 29 in the cannula. The distal tip is closed, but is preferably fluid permeable. The advantage of the "pulling" mechanism is that the final distal position of the cannula tip is unchanged by the deployment. This is advantageous where one needs to know the location of the distal end relative to an in vivo structure.

The present invention provides a method of inserting and using the cannulae of the present invention. One such method comprises the steps of A method of stenting a vessel while permitting fluid flow, comprising the steps of: providing an expandable cannula comprising, an inner tube having a proximal end and a distal end, at least a portion of which is fluid impermeable; an outer tube having a proximal end and a distal end, at least a portion of which is fluid permeable, the inner tube fitting within at least a portion of the outer tube; at least a portion of the outer tube being expandable from a constricted state having a first diameter to a natural state having a second diameter, the outer tube when in the natural state being expandable to substantially the same diameter of the inner wall of a vessel in which the expandable cannula can be inserted; inserting the expandable cannula through an opening in the vessel; permitting the outer tube to expand from constricted state to a natural state such that at least a substantial portion of the outer tube expanding to have a diameter substantially the same as or greater than the diameter of the vessel inner wall so as to stent at least a portion of the vessel open; permitting fluid to flow from the outer tube distal end toward the direction of the outer tube proximal end and into the distal end of the inner tube.

The steps of the above method can be applied to various structural embodiments of the present invention.

The present invention also provides a kit containing an introducer needle, cannula according to one of the embodiments of the present invention as described above, and, optionally, an actuator comprising a guidewire, trocar or the like.

Other possible applications of the present invention include, but are not limited to, VADs. ECMO cannula vents/cardioplegia cannula, vacuum-assisted venous drainage, chest tubes, pediatric, minimally invasive procedures, ambulatory care, suction instruments, abscess drainage, subcutaneously tunneled access lines, and intravenous peripheral access needles. Nonmedical applications are also contemplated as being within the scope of the present invention, such as, but not limited to fluid introduction into chemical or cooking processes where fluid dynamics must be controlled, fuel injection engines where particle filtration is of concern, and the like.

Advantages

The general design feature of a cannula with an expandable wall is referred to as a "dynamic radius". This property is shared by all cannulae described in this patent application and therefore are referred to as the "dynamic cannula" group to conceptually separate them from traditional cannula with non-expandable walls. Another distinction between these cannulae and traditional cannulae is the potential for the dynamic cannula to act as a fluid-permeable stent, allowing the vessel itself to act as a conduit.

The design features may benefit the patient population by advancing the technology of aortic/arterial cannula, venous cannula, specialized vascular access devices, and other miscellaneous applications. Design features include dynamic radius, funneling, occlusion, filtering, thin-walled, and close-ended properties. Design features further include funneling, double-layered cannula, open-ended cannula deployment, and pulling versus pushing cannula deployment configurations and mechanisms.

An arterial cannula with an expandable dynamic radius permits the cannula to expand to fill the endovascular space. An increase in the dynamic cannula's internal diameter compared to traditional cannula significantly improves the flow through the cannula by decreasing the resistance of fluid passing through the cannula. The clinical impact of this effect may be to improve arterial perfusion during cardiopulmonary bypass, allow use of minimally invasive or peripheral limb approaches to cannulation, The dynamic radius and the close-ended/internal deployment mechanism may reduce trauma to blood vessels due to the narrow insertion profile and compliancy of cannula walls following deployment than traditional cannula. The compressible and expandable nature of the cannula walls may provide easier placement into vessels for the user due to the cannula's narrower insertion profile and reduced risk of dislodgement or bleeding following deployment due to the radial force exerted by the cannula on surrounding tissues. Since the cannula may "custom-fit" to the inner diameter of a blood vessel, a single size diameter dynamic cannula functions in a broader range of vessels diameters. This may simplify cannula size selection for the user and significantly reduced hospital inventory of various cannula sizes. Alternatively, other embodiments of the cannula purposefully do not completely occlude the vessel. The double-layered cannula design may help overcome the problem of distal limb ischemia by providing distal flow during prolonged arterial cannulation.

The funneled-tip for aortic cannulation during cardiopulmonary bypass may improves the fluid dynamics as described in detail in prior disclosures. The properties of funneling and/or filtering may decrease the risk of artherosclerotic plaque embolization and associated stroke. In one embodiment, the specialized aortic cannula's ability to completely occlude the endovascular space without migrating, may eliminate the need for secondary clamps or balloons to provide isolation of the heart during cardiopulmonary bypass.

The cannula's flexible dynamic radius body may provide improved access to tortuous vasculature. The pulling mechanism of deployment may potentiate passage of cannula through tortuous, branching, or tight vascular spaces. This may help the cannula reach its final anatomical location by enabling the cannula to be positioned in a more malleable, less rigid state (not-full elongated, not fully narrowed).

The dynamic radius, funneling, and/or double-layered cannula configurations may increase the effective orifice area of venous cannula and improve venous drainage during cardiopulmonary bypass surgery. In minimally invasive surgery and peripheral venous cannulation, this may reduce or eliminate the need for vacuum and its associated problems. The funneling can improve fluid dynamics by selectively dilating a compliant vessel such as a vein. The stenting effect can be varied as to anatomical location and the degree of radial expansion of the vessel. The double-layered cannula may improve drainage of side vessels. The double-layered cannula design also offers the potential to improve fluid dynamics by significantly shortening the conduit component of the cannula. The double-layered cannula allows the conduit portion to be repositioned at any point during a procedure with less trauma and disruption. The improved fluid dynamic effect of these features and the close-ended deployment mechanism to ease insertion may increase the surgical options for vessel cannulation sites (e.g. during cardiopulmonary bypass, transfer venous cannulation to a peripheral jugular vein approach in the patient's neck and free the surgical field from visual and mechanical obstruction due to cannulation of the heart directly through the atrial appendage).

In application to the technology of peripheral IV catheters, the dynamic radius design provides rapid IV fluid infusion and may increase the rate of successful and secure IV line placement.

The application of a dynamic radius combined with an open-ended deployment to the technology of "introducers" (commonly used in cardiology for angiography) would enable a greater cross-sectional area in the vessel with an open cannula tip that would improve fluid flow and ease the passage of instruments. The advances of this may be to have a smaller puncture hole in the artery and decrease bleeding from the alteriotomy site, eliminate the need for the Seldinger technique (due to the narrow insertion size), safer and less traumatic dilation of the surrounding tissues (dilation is performed within the confines of the cannula).

The application of a dynamic radius with an open-ended configuration to thoracostomy ("chest tubes") may reduce the patient morbidity and mortality associated with chest tube placement for pneumo- and hemo-thoraxes. These design features allow the immediate placement of a percutaneous narrow profile chest tube (needle-size) which can be safely converted to a larger diameter tube. These features could also be exploited in expandable instrument ports for endoscopic surgery. Given the increase in fluid flow and decrease in tissue trauma attributable to these cannula design characteristics, the drainage of highly viscous fluids such as in abscess drainage catheters may benefit from this technology. A specialized dynamic cannula may enable abscesses to be drained percutaneously and decrease the patient morbidity associated with traditional surgical incision and drainage.

Finally, suction devices designed using the dynamic radius and a double-layer design may be inserted in a narrower profile to reach previously unattainable positions and improve suctioning ability by stenting tissue away from the drainage orifices in the cannula.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

The invention claimed is:

1. An expandable cannula having a first state having a constricted diameter and a second state having an expanded diameter for at least a portion of its length, said cannula comprising:
a tube comprising a material that enables the diameter along at least a portion of its length to increase radially from the first state to the second state, said tube having
i) a wall enclosing a lumen;
ii) a proximal end; and
iii) a distal end;
wherein the wall of at least a portion of the tube of the cannula in the second state gradually flares from the constricted diameter to the expanded diameter at an angle of up to 20 degrees from a central axis of the tube to form a funnel shape.

2. The expandable cannula of claim 1, wherein at least a portion of said tube is fluid impermeable coating.

3. The expandable cannula of claim 1, wherein at least a portion of said tube is at least partially fluid permeable.

4. The expandable cannula of claim 1, wherein at least a portion of the inside of said tube is coated with a first coating and at least a portion of the outside of said tube is coated with a second coating.

5. The expandable cannula of claim 1, further comprising a joining of expandable materials at one end.

6. The expandable cannula of claim 1, further comprising an end cap.

7. The expandable cannula of claim 6, wherein the end cap is solid.

8. The expandable cannula of claim 6, wherein the end cap has an opening defined therein.

9. The expandable cannula of claim 1, wherein the tube of the cannula in the second state gradually tapers from the expanded diameter to a smaller diameter.

10. The expandable cannula of claim 1, wherein said tube is self-expanding.

11. The expandable cannula of claim 1, wherein said tube expands in response to a mechanical force.

12. The expandable cannula of claim 1, wherein said tube contracts in response to a mechanical force.

13. The expandable cannula of claim 1, wherein said tube expands in response to an electrical stimulus.

14. The expandable cannula of claim 1, wherein said tube contracts in response to an electrical stimulus.

15. The expandable cannula of claim 1, wherein said tube expands in response to a thermodynamic stimulus.

16. The expandable cannula of claim 1, wherein said tube contracts in response to a thermodynamic stimulus.

17. The expandable cannula of claim 1, wherein the material comprises a mesh material.

18. The expandable cannula of claim 1, wherein the material comprises a biodegradable material.

19. The expandable cannula of claim 1, wherein the wall of at least a portion of the tube of the cannula in the second state gradually flares from the constricted diameter to the expanded diameter at an angle of up to about 7 degrees from the central axis of the tube.

20. The expandable cannula of claim 1, wherein said flared portion, when positioned within a vessel having an internal wall having a diameter, substantially expands to said internal wall diameter.

21. The expandable cannula of claim 1, wherein the material of at least a portion of said tube comprises a wire mesh material.

22. A method of stenting a vessel while permitting fluid flow, the method comprising:
   a. providing an expandable cannula of claim 1
   b. inserting said expandable cannula through an opening in said vessel;
   c. permitting said cannula to expand from the first state to the second state; and
   d. permitting fluid to flow through said tube.

23. A method of cannulating a vessel, the method comprising:
   a. providing an expandable cannula of claim 1;
   b. providing a trocar having a proximal end and a distal end;
   c. inserting said trocar into said tube so that said trocar distal end contacts at least a portion of said wall of said tube at the distal end;
   d. introducing said tube and trocar into a vessel; and
   e. permitting said cannula to expand from the first state to the second state, thereby cannulating the vessel.

24. A blood vessel access kit, comprising:
   a. a needle;
   b. an actuator comprising an elongated member; and
   c. an expandable cannula of claim 1.

25. The expandable cannula of claim 1, wherein said material comprises a shape memory material.

26. The expandable cannula of claim 1, wherein said material comprises a metal, ceramic, or polymer.

27. The expandable cannula of claim 1, wherein said material comprises nitinol or stainless steel.

28. The expandable cannula of claim 1, wherein an inner side of said wall comprises grooves or ribs.

29. The expandable cannula of claim 1, wherein the flared portion of the wall flares in a straight line.

30. The expandable cannula of claim 1, wherein the flared portion of the wall flares in a curved line.

31. The expandable cannula of claim 1, wherein the gradual flare provides a decrease in exit velocity of fluid passing through the cannula compared to a cannula of the same constricted diameter without the funnel shape.

32. The expandable cannula of claim 1, wherein the wall flares from the distal end towards the proximal end.

33. The expandable cannula of claim 1, wherein the wall flares from the proximal end towards the distal end.

34. The expandable cannula of claim 1, further comprising a trocar having a diameter sized to fit within said tube and attached to a distal end of the tube.

35. The method of claim 23, wherein permitting said cannula to expand from the first state to the second state comprises removing said trocar such that said cannula tube radially expands to said second state.

36. The method of claim 23, wherein permitting said cannula to expand from the first state to the second state comprises leaving the trocar in place and releasing a temporary attachment of the proximal end of the tube to a proximal end of the trocar such that said cannula tube radially expands to said second state.

* * * * *

UNITED STATES PATENT AND TRADEMARK OFFICE
CERTIFICATE OF CORRECTION

| | |
|---|---|
| PATENT NO. | : 7,799,046 B2 |
| APPLICATION NO. | : 10/498442 |
| DATED | : September 21, 2010 |
| INVENTOR(S) | : Jennifer White |

It is certified that error appears in the above-identified patent and that said Letters Patent is hereby corrected as shown below:

Column 15,
Line 2, delete "coating"

Column 15,
Line 52, after "claim 1" insert --;--

Signed and Sealed this
Eighth Day of February, 2011

David J. Kappos
*Director of the United States Patent and Trademark Office*